United States Patent [19]

Zucker et al.

[11] 4,336,203

[45] Jun. 22, 1982

[54] PROCESS FOR THE CONTINUOUS PRODUCTION OF ALKALI METAL SALTS OF FATTY ACIDS

[75] Inventors: Friedrich J. Zucker, St. Andreas-Strasse 16, D-4040 Neuss 21; Georg Osthaus; Paul Plassmann, both of Neuss, all of Fed. Rep. of Germany

[73] Assignee: Friedrich J. Zucker, Neuss, Fed. Rep. of Germany

[21] Appl. No.: 218,568

[22] Filed: Dec. 22, 1980

Related U.S. Application Data

[63] Continuation of Ser. No. 90,044, Oct. 31, 1979, abandoned.

[30] Foreign Application Priority Data

Nov. 2, 1978 [DE] Fed. Rep. of Germany ....... 2847457

[51] Int. Cl.³ ................................................ C11C 1/04
[52] U.S. Cl. ..................................... 260/417; 252/369
[58] Field of Search .......................... 260/413 S, 417; 252/369

[56] References Cited

U.S. PATENT DOCUMENTS 2,730,539 1/1956 Bradford ............................ 260/417
3,657,146 4/1972 Fransen et al. ..................... 260/417
4,060,535 11/1977 Cinco ............................... 260/413 S

*Primary Examiner*—John F. Niebling
*Attorney, Agent, or Firm*—Max Fogiel

[57] ABSTRACT

Alkali metal salts of fatty acids or soaps are produced in a continuous process by reacting a fatty acid or fatty acid mixture with an alkali metal hydroxide in the shear field of a rotor-stator machine with interengaging radial surfaces. The reaction occurs in the absence or presence of up to a maximum of 15% by weight of solvent optionally in the presence of other additives of the type normally used in the manufacture of soap. The reaction product is run off as a graulate or a strand like product.

10 Claims, No Drawings

PROCESS FOR THE CONTINUOUS PRODUCTION OF ALKALI METAL SALTS OF FATTY ACIDS

This is a continuation, of application Ser. No. 90,044 filed Oct. 31, 1979, abandoned.

BACKGROUND OF THE INVENTION

The present invention relates to a process for the continuous production of alkali metal salts of fatty acids.

Alkali metal salts of fatty acids, or what are commonly known as soaps, can be obtained from fatty acid esters of glycerine or from fats or from fatty acids by reaction with alkali metal hydroxides. There are several known batch-type processes and continuous processes for the production of soaps. The batch-type processes are generally carried out at boiling point in an open stirrer-equipped vessel. In the case of the continuous processes, saponification in closed vessels has already been successfully applied in some cases, especially since it provides for a considerable reduction in energy costs. However, the known processes, including the continuous process, are still attended by serious disadvantages. Not only do the products obtained have a very high water content due to the fact that saponification is carried out in emulsion, the water having to be removed by evaporation. (in some cases even in vacuo,) but also by the fact that the aqueous phase which accumulates during centrifuging of the soap emulsion also has to be worked up. Both process steps involve (in some cases serious) effluent problems and, in addition, are also costly in regard to the energy required for working up.

Accordingly, there was a genuine need to develop a process for the production of alkali salts of fatty acids which not only can be carried out continuously using reaction components present in concentrated form, but also yields end products which do not require any further drying.

SUMMARY OF THE INVENTION

According to the present invention, this need is satisfied by a process for the continuous production of alkali metal salts of fatty acids by reacting a fatty acid or fatty acid mixture with an alkali metal hydroxide, optionally in the presence of other additives of the type normally used in the manufacture of soap. The reaction mixture is reacted in the absence or presence of up to a maximum of 15% by weight of solvent in the shear field of a rotor-stator machine having interengaging radial surfaces. The reaction product is run off in the form of a granulate or product strand.

The process according to the present invention is preferably carried out by introducing at least one of the reaction components under pressure into the reaction zone. The fatty acid or fatty acid mixture and the alkali metal hydroxide may be used in stoichiometric quantities, although it is also possible to use one of the reaction components in excess.

As already mentioned, the reaction mixture is reacted in the shear field of a rotor-stator machine either in the absence of solvents or even in the presence of solvents, preferably water, providing the quantity of solvent does not exceed 15% by weight. The reaction of the reaction components in the shear field of the machine takes place at a very high velocity and is generally over in fractions of a second. The residence time of the reaction mixture is best limited to less than 2 seconds.

Where the reaction is carried out at relatively high temperatures, for example at temperatures above 100° C., solvent additionally evaporates from the reaction product, although even where the process is carried out normally there is no need for the reaction products to be dried.

DESCRIPTION OF THE PREFERRED EMBODIMENTS

The process according to the invention is illustrated by the following Examples.

EXAMPLE 1

A machine of the rotor-stator type, as for example, Supraton machine, comprising a rotor rotating in a housing of which the outer surface is equipped with coaxial rings of staggered diameter which interengage with identical rings on the stator, for example, the inner housing wall, opposite the rotor, is continuously charged by pumping with a 50% by weight sodium hydroxide solution and a fatty acid mixture having an average molecular weight of 280 (ratio of fatty acid mixture to sodium hydroxide solution 1:0.285) in separate streams at a temperature of 50° C., after which this mixture reacts in fractions of a second in the shear field of the machine to form the sodium salts of the fatty acid used which may be run off.

EXAMPLE 2

280 kg of a fatty acid mixture having an average molecular weight of 280 are premixed with 40 kg of solid sodium hydroxide and again delivered continuously to the shear field of the machine described in Example 1 by means of a positive conveyor, such as a pump or a positive screw conveyor. At the same time, water is continuously added (ratio of fatty acid/alkali mixture to water 1:0.12). The sodium soap obtained as reaction product in this case contains approximately 15% by weight of water.

EXAMPLE 3

The procedure is the same as in Example 2, except that the water is added in a quantity corresponding to a ratio of fatty acid/alkali mixture to water of 1:0.06. In this case, the sodium salts of the fatty acids used are obtained in the form of a mixture having a total water content of approximately 10% by weight. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed is:

1. A process for the continuous production of alkali metal salts of fatty acids comprising the steps of: reacting a fatty acid mixture with an alkali metal hydroxide in stoichiometric quantities, optionally in the presence of other additives of the type normally used in the manufacture of soap; reacting the reaction mixture in the absence or presence of up to a maximum of 15% by weight of solvent in the shear field of a rotor-stator machine with interengaging radial surfaces; running off the reaction product in the form of a granulate or product strand, said rotor-stator machine producing forces for immediate spontaneous conversion of continuously supplied reaction components without substantial delay; producing shear forces, peripheral elastic forces, micro-cavitation, and ultrasonic alternating pulses from compression and decompression for affecting the reaction, the reaction being spontaneous and exothermic, mixing and reacting occurring substantially simultaneously; and cooling the reaction product evaporatively by reaction water vaporization to avoid discolorization, said product leaving the reaction zone in form of a substantially small aggregate with a substantially high degree of capillaries.

2. A process as defined in claim 1, wherein at least one component of the reaction mixture is delivered under pressure.

3. A process as defined in claim 1, wherein the residence time of said reaction mixture in said shear field is limited to less than 2 seconds.

4. A process as defined in claim 1, wherein the reaction is carried out at relatively high temperatures and solvent is evaporated off from said reaction product.

5. A process as defined in claim 1, wherein said rotor-stator machine is continuously charged by pumping with a 50% by weight sodium hydroxide solution and a fatty acid mixture having an average molecular weight of 280 in separate streams at a temperature of 50° C., the ratio of fatty acid mixture to sodium hydroxide solution being 1:0.285, the mixture reacting thereafter in fractions of a second in the shear field to form sodium salts of the fatty acid used which may be run off.

6. A process as defined in claim 5, wherein 280 kg of a fatty acid mixture having an average molecular weight of 280 are premixed with 40 kg of solid sodium hydroxide and delivered continuously to the shear field, water being continuously added at the same time, the ratio of fatty acid/alkali mixture to water being 1:0.12, the reaction product being sodium soap containing substantially 15% by weight of water.

7. A process as defined in claim 1, wherein 280 kg of a fatty acid mixture having an average molecular weight of 280 are premixed with 40 kg of solid sodium hydroxide and delivered continuously to the shear field, water being continuously added at the same time, the ratio of fatty acid/alkali mixture to water being 1:0.06, sodium salts of the fatty acids resulting in form of a mixture having a total water content of substantially 10% by weight.

8. A process as defined in claim 1, wherein said process is substantially free of high temperatures and pressures to avoid damage to the product.

9. A process as defined in claim 1, wherein at least one component of the reaction mixture is delivered under pressure, the residence time of said reaction mixture is delivered under pressure, the residence time of said reaction mixture in said shear field being limited to less than two seconds, the reaction being carried out at relatively high temperatures and solvent being evaporated off from said reaction product.

10. A process as defined in claim 1, wherein at least one component of the reaction mixture is delivered under pressure, the residence time of said reaction mixture is delivered under pressure, the residence time of said reaction mixture in said shear field being limited to less than two seconds, the reaction being carried out at relatively high temperatures and solvent being evaporated off from said reaction product, said rotor-stator machine being continuously charged by pumping with a 50% by weight sodium hydroxide solution and a fatty acid mixture having an average molecular weight of 280 in separate streams at a temperature of 50° C., the ratio of fatty acid mixture to sodium hydroxide solution being 1:0.285, the mixture reacting thereafter in fractions of a second in the shear field to form sodium salts of the fatty acid used which may be run off.

* * * * *